(12) United States Patent
Wang et al.

(10) Patent No.: US 6,329,174 B1
(45) Date of Patent: Dec. 11, 2001

(54) NUCLEIC ACID ENCODING LEPIDOTERAN GLUTAMATE-GATED CHLORIDE CHANNEL

(75) Inventors: Xiao-Zhuo Michelle Wang, Chapel Hill, NC (US); Xavier Georges Sarda, Sainte Genevieve des Bois (FR); Michael David Tomalski, Raleigh; Vincent Paul Mary Wingate, Chapel Hill, both of NC (US)

(73) Assignee: Aventis Cropscience SA, Lyons Cedex (FR)

( * ) Notice: Subject to any disclaimer, the term of this patent is extended or adjusted under 35 U.S.C. 154(b) by 0 days.

(21) Appl. No.: 09/592,891

(22) Filed: Jun. 13, 2000

(51) Int. Cl.⁷ ............... C12N 5/10; C12N 15/12; C12N 15/63; C12N 15/64; C07K 14/705
(52) U.S. Cl. ............ 435/69.1; 536/23.1; 536/23.5; 435/71.1; 435/71.2; 435/471; 435/325; 435/320.1; 435/252.3; 435/254.11; 530/350
(58) Field of Search .................. 536/23.1, 23.5; 530/350; 435/69.1, 71.1, 71.2, 471, 325, 320.1, 252.3, 254.11

(56) References Cited

U.S. PATENT DOCUMENTS 5,527,703    6/1996    Cully et al. .
5,693,492    12/1997   Cully et al. .

OTHER PUBLICATIONS

Arena et al. (1991) Molecular Pharm. 40:368.

Arena et al. (1992) Molecular Brain Research 15:330.

Cully et al. (1994) Nature 371:707.

Cully et al. (1996) J. Biol. Chem 271:20187.

Delany et al. (1998) Mol. Biochem Parasit 97:177.

Mikayama et al. Proc. Natl. acad. Sci. USA. vol. 90, pp. 10056–10060, 1993.*

Voet et al. Biochemistry. John Wiley & Sons, Inc., pp. 126–128 and 228–234, 1990.*

* cited by examiner

*Primary Examiner*—Prema Mertz
(74) *Attorney, Agent, or Firm*—Baker Botts L.L.P.

(57) ABSTRACT

The present invention is directed to a nucleic acid encoding a lepidopteran glutamate-gated chloride channel. Vectors and host cells comprising the nucleic acid are also provided. A method of identifying agents that modulate the activity of a lepidopteran glutamate-gated chloride channel is also provided. Such agents are useful as insecticides.

17 Claims, 1 Drawing Sheet

NUCLEIC ACID ENCODING LEPIDOTERAN GLUTAMATE-GATED CHLORIDE CHANNEL

BACKGROUND OF THE INVENTION

Glutamate-gated chloride channels are a family of ligand-gated chloride channels unique to invertebrates. Glutamate-gated chloride channels have been cloned from *Caenorhabditis elegans* (Cully et al. (1994) Nature 20:371; U.S. Pat. No. 5,527,703), *Drosophila melanogaster* (Cully et al. (1996) J. Biol. Chem. 271:20187 and U.S. Pat. No. 5,693,492), *Haemonchus contortus* (Delany et al. (1998) Mol. Biochem. Parasit. 97:177), *Lucilia cuprina* (GenBank Accession No. AAC31949) and *Schistocerca americana* (Cohen et al. (1999) 29th Annual Neuroscience Meeting, p. 199). The clones isolated from *C. elegans, D. melanogaster* and *S. americana* have been functionally expressed in *Xenopus oocytes*, and shown to be activated by glutamate and avermectin. (Arena et al. (1991) Molecular Pharm. 40:368; Arena et al. (1992) Molecular Brian Research 15:339; U.S. Pat. No. 5,693,492; U.S. Pat. No. 5,527,703; Cohen et al., supra).

Because glutamate-gated chloride channels are specific to invertebrates, the channels provide a target for insecticides. In particular, the glutamate-gated chloride channels are the target of the avermectin class of insecticides. Avermectins are naturally occurring and synthetic marocylic lactones that are widely used in the treatment of parasites and insects.

Insects of the order lepidoptera are significant pests, and in particular the larvae are destructive defoliaters. Further, lepidopteran pests are typically harder to control than diptera. According, there is a need to identify and develop safe and specific insecticides against lepidopteran pests. The present invention address this need by providing isolated nucleic acids encoding a lepidopteran glutamate-gated chloride channel, recombinant lepidopteran glutamate-gated chloride channels, and a method of identifying agents that modulate the activity of the channel.

SUMMARY OF THE INVENTION

The present invention is directed to an isolated nucleic acid encoding a lepidopteran glutamate-gated chloride channel. In a preferred embodiment the nucleic acid is isolatable from *Heliothis virescens*. In another preferred embodiment the nucleic acid comprises a sequence encoding the amino acid sequence of SEQ ID NO. 14.

The present invention further comprises vectors comprising a nucleic acid encoding a lepidopteran glutamate-gated chloride channel, and hot cells comprising the vectors.

Another aspect of the present invention provides a recombinant lepidopteran glutamate-gated chloride channel, and kits and compositions comprising a recombinant lepidopteran glutamate-gated chloride channel. A method for preparing a lepidopteran glutamate-gated chloride channel is also provided.

In yet another embodiment, the present invention provides a *Xenopus oocyte* comprising a nucleic acid encoding a lepidopteran glutamate-gated chloride channel, and a *Xenopus occyte* expressing a functional lepidopteran glutamate-gated chloride channel.

The present invention further provides a method of identifying agents that modulate the activity of the lepidopteran glutamate-gated chloride channel, and agents identified by the method.

DETAILED DESCRIPTION OF THE INVENTION

Figure 1:
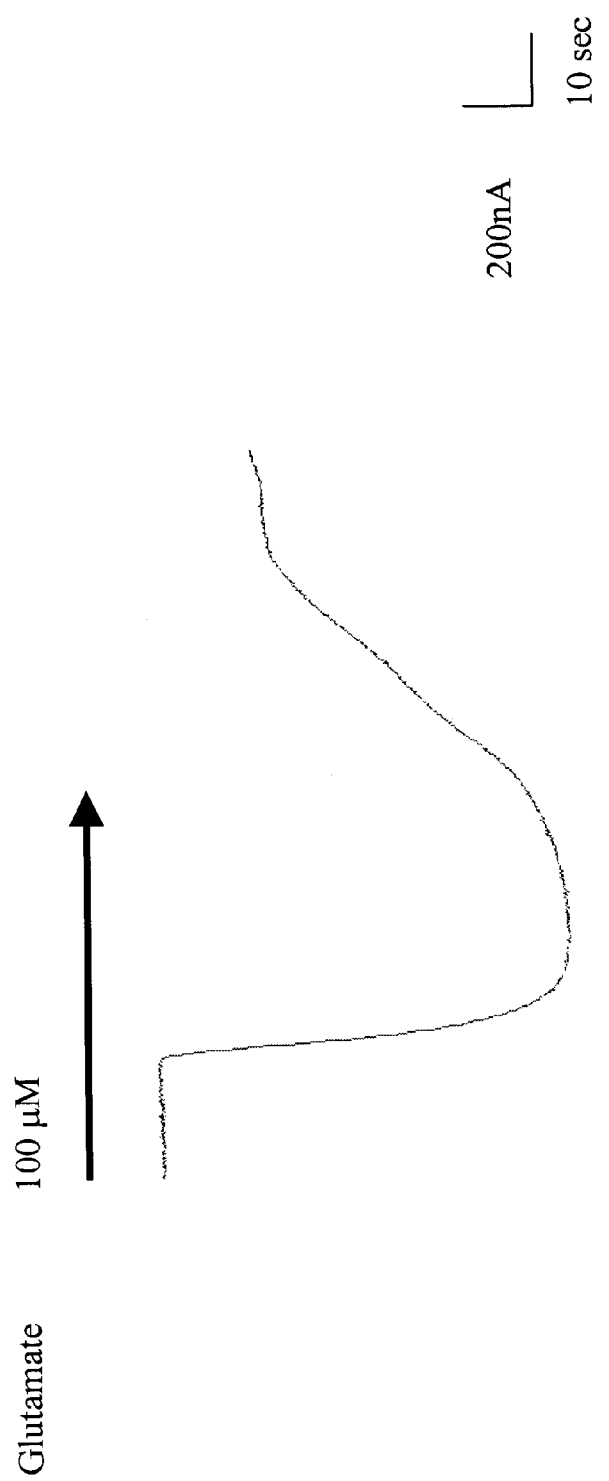
FIG. 1 presents electrophysiological recordings demonstrating the effect of glutamate on a lepidopteran glutamate-gated chloride channel expressed in *oocytes*.

The present invention is directed to isolated nucleic acids encoding lepidopteran glutamate-gated chloride channels. An isolated nucleic acid encoding a lepidopteran glutamate gated chloride channels is defined herein as a nucleic acid isolatable from an insect of the order *lepidoptera* and capable of encoding a functional glutamate-gated chloride channel. In a preferred embodiment, the nucleic acid is isolatable from Heliothis. In a more preferred embodiment, the nucleic acid is isolatable from *Heliothis virescens*. A functional glutamate-gated chloride channel is defined herein as a protein having the ability to bind glutamate and thereby mediate chloride flux in a cell expressing the channel.

The isolated nucleic acid may be DNA or RNA, including cDNA and mRNA. In a preferred embodiment, the isolated nucleic acid has a sequence encoding the amino acid sequence of SEQ ID NO. 14. The ordinarily skilled artisan, with knowledge of the genetic code, can determine DNA and RNA sequences that encode the amino acid sequence set forth in SEQ ID NO. 14. Further, the sequence may be selected to optimize expression in a particular host organism by utilizing known preferred codons for the host organism of choice.

In another preferred embodiment, the isolated nucleic acid comprises the sequence set forth in SEQ ID NO.13. In another preferred embodiment, the isolated nucleic acid comprises the sequence of nucleotides 144 through 1484 of SEQ ID No. 13. Fragments of nucleic acid having the sequence of SEQ ID No. 13 that maintain the ability to encode a functional lepidopiteran glutamate-gated chloride channel are also encompassed by the present invention.

The present invention further encompasses nucleic acids isolatable from *lepidoptera* and capable of hybridizing under high stringency conditions to the complement of a nucleic acid having the sequence of nucleotides 144 through 1484 of SEQ ID NO: 13. Nucleic acid hybridization conditions are known to those of ordinary skill in the art and disclosed for example by Sambrook et al. (1989) Molecular Cloning—A laboratory manual, Cold Spring Harbor Laboratory Press. High stringency conditions are defined herein as 0.1X standard saline citrate (SSC), 0.1% sodium dodecyl sulfate (SDS) at 60° C.

In another embodiment, the present invention provides isolated nucleic acids having at least about 80%, and preferably at least about 90%, and more preferably at least about 95% sequence identify to the nucleic acid having the sequence of nucleotides 144 through 1484 of SEQ ID NO: 13. Sequence identity is determined using the program Clustal W described by Higgins et al. (1994) Nucleic Acids Res. 22:4673 and may be calculated using the EMBL Nucleotide Sequence Database (http://www.ebi.ac.uk/embl.html). The ability of the isolated nucleic acid of the present invention to encode a functional glutamate-gated chloride channel can be determined by functional assays as described hereinbelow.

A protein having the amino acid sequence of SEQ ID NO: 14 has glutamate-gated chloride channel activity. Analysis of the amino acid sequence and alignment with the sequence of the Drosophila glutamate-gated chloride channel indicates that the sequence of SEQ ID NO: 14 contains four membrane spanning regions at amino acids 246–268, 274–293, 309–328 and 415–435. The amino terminal 20–30 amino acids encode a signal peptide. Amino acid changes may be tolerated in the signal peptide domain so long as the ability of the protein to insert into a selected cell membrane is maintained. Those or ordinary skill in the art can determine suitable modifications of the sequence of the signal peptide and can likewise determine the nucleic acid sequence encoding the modified signal peptide domain.

The nucleic acids of the present invention may be obtained by using a nucleic acid having the sequence of SEQ ID NO: 13 or a fragment thereof to probe a lepidopteran cDNA library. Such libraries may be made by well-known methods, described for example in Sambrook et al., supra, or may be obtained commercially. The identity of the nucleic acid may be confirmed by nucleotide sequencing or by expression and functional analysis as described hereinbelow.

The present invention is further directed to vectors comprising the isolated nucleic acids of the present invention. In the vectors of the present invention, the nucleic acid encoding a lepidopteran glutamate-gated chloride channel is operably linked to suitable transcriptional and/or translational regulatory elements to effect expression of the glutamate-gated chloride channel in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one or ordinary skill in the art, and vectors into which the nucleic acid of the invention can be inserted are also commercially available. Recombinant viral vectors, including retrovirus, baculovirus, paravovirus and densovirus vectors are particularly preferred.

In a preferred embodiment the vector comprises a strong constitutive or inducible promoter operably linked to a nucleic acid encoding a lepidopteran glutamate-gated chloride channel. Suitable promoters are well known and readily available to one or ordinary skill in the art, and include for example, the polyhedrin promoter (Kitts et al., 1993, Bio Techniques, 14:810), heat shock promoter (Stellar et al., 1985, EMBO J., 4:167) and metallothionein promoter (Kaufman et al., 1989, Cell 59:359). Expression vectors can be constructed by well known molecular biological methods as described, for example, in Sambrook et al. (1989) Molecular Cloning: A Laboratory Manual, Cold Spring Harbor Laboratory Press, Cold Spring Harbor, N.Y., or any of a myriad of laboratory manuals on recombinant DNA technology that are widely available. Expression vectors into which the nucleic acids of the present invention can be cloned under the control of a suitable promoter are also commercially available.

Another embodiment of the present invention provides host cells containing the vectors described above. The host cell may be procaryotic or eukaryotic, including bacterial, yeast, insect or mammalian. Insect and mammalian cells are preferred. Particularly preferred host cells include insect cell lines, including for example Spodoptera frugiperda cells. The host cells may be transformed, transfected or infected with the expression vectors of the present invention by methods well-known to one of ordinary skill in the art. Transfection may be accomplished by known methods, such as liposome mediated transfection, calcium phosphate mediated transfection, microinjection and electroporation. Permanently transformed insect cell lines are particularly preferred. For example, insect cell lines such as Drosophilia cell line SH1 can be transformed with the expression vectors of the present invention by commercially available lipofectin (GIBCO-BRL) to provide permanently transformed cell lines expressing a functional glutamate-gated chloride channel. In a preferred embodiment, the vector is designed such that expression of the protein is inducible.

Expression systems utilizing baculovirus vectors and insect host cells are preferred. The use of baculoviruses as recombinant expression vectors to infect lepidopteran insect cells is known in the art and described for example by Luckow et al. (1988) Bio/Technology 6:47–55 and Miller (1988) Ann Rev Microbiol. 42:177–199. The baculovirus vectors generally contain a strong baculovirus promoter operably linked to a nucleic acid of the present invention such that the promoter directs expression of the lepidopteran glutamate-gated chloride channel Baculovirus polyhedrin promoters such as the *Autographa californica* nuclear polyhydrosis virus polyhedrin promoter are preferred.

The baculovirus expression vectors of the present invention are made by inserting the nucleic acid encoding the lepidopteran glutamate-gated chloride channel downstream of the polyhedrin promoter in a baculovirus transfer vector, for example pBacPac8 available from Clontech or Bac-to-Bac available from Life Technologies. Baculovirus transfer vectors further contain flanking baculovirus sequences that allow homologous recombination between the transfer vector and baculovbirus DNA during co-transfection. The transfer vector containing the nucleic acid of the invention and viral DNA are used to co-transfect insect cells. In a preferred embodiment the insect cells are Spodoptera. *Spodoptera frugiperda* cells including Sf9 are particularly contemplated During co-transfection, homoogous recombination results in the transfer of an expression cassette containing the polyhedrin promoter and the nucleic acid of the present invention to the polyhedrin locus of the viral DNA. The resulting recombinant virus is used to generate viral stocks by standard methods. Insect host cells are infected with the recombinant virus to produce insect cells expressing the glutamate-gated chloride channel.

The present invention is further directed to recombinant glutamate-gated chloride channel. The recombinant lepidopterant glutamate gated chloride channel may be isolated in a membrane preparation or present in the cell membrane of the host cell in which it has been recombinantly produced. Whole cells and membrane preparations comprising the recombinant lepidopteran glutamate-gated chloride channel are particularly contemplated. Recombinant lepidopteran glutamate-gated chloride channel is useful, for example, to screen potential insecticides by specific bonding assays or functional assays.

The present invention further provides a method of making recombinant lepidopteran glutamate-gated chloride channel. Recombinant lepidopteran glutamate-gated chloride channel is made by transforming, transfecting or infecting a suitable host cell with an expression vector comprising a nucleic acid encoding a lepidopteran glutamate-gated chloride channel, culturing the host cell under conditions suitable for expression, and optionally recovering the recombinant lepidopteran glutamate-gated chloride channel. A suitable host cell is any cell in which the nucleic acid encoding the transporter can be expressed to provide a functional glutamate-gated chloride channel. In a preferred embodiment, the recombinant lepidopteran glutamate-gated chloride channel is made in insect cells, preferably *Spodoptera frugiperda* 9 (Sf9), by infecting the insect cells with a recombinant virus in which the nucleic acid of the invention is under the control of a promoter suitable for use in Sf9 cells, such as a polyhedrin or TE1 promoter, and culturing the cells under conditions suitable for expression of the recombinant lepidopteran glutamate-gated chloride channel. In another preferred embodiment, the recombinant lepidopteran glutamate-gated chloride channel is made in permanently transformed cell lines as described above.

A functional lepidopteran glutamate-gated chloride channel can be identified by one of ordinary skill in the art by functional assays. An exhaustive review of techniques and protocols is provided in Rudy et al., eds (1992) Methods in Enzymology 207, Academic Press, Inc., San Diego, Calif. For example, two-electrode voltage clamp recordings of host cells or *oocytes* expressing the lepidopteran glutamate-gated chloride channel can be used to assess chloride flux in response to application of glutamate or ivermectin phosphate. Dose-dependent glutamate-evoked currents indicate the presence of a functional glutamate-gated chloride channel. Also, the activation of a membrane current by about 100 μm glutamate or 1 μm ivermectin phosphate is indicative of a functional glutamate-gated chloride channel.

The present invention further provides an amphibian *oocyte* comprising a nucleic acid encoding a functional glutamate-gated chloride channel, and an amphibian *oocyte* expressing a functional glutamate-gated chloride channel. The *oocytes* are useful as a system for screening potential insecticides useful against insects of the order *lepidoptera*. Such *oocytes* can be made using the nucleic acids of the invention and methods known in the art. In a preferred embodiment, the *oocyte* is *Xenopus laevis oocyte*. For example, expression vectors containing cDNA encoding the glutamate-gated chloride channel under the control of a strong promoter can be injected into the nuclei of *oocytes*, after which *oocytes* are incubated for from one to several days, followed by assessment for the presence of functional glutamate-gated chloride channel. Alternatively, mRNA can be synthesized in vitro from cDNA encoding the glutamate-gated chloride channel, and injected into *oocytes,* followed by assessment for the presence of functional glutamate-gated chloride channels as described hereinabove.

The present invention further provides methods of identifying agents that modulate the activity of a lepidopteran glutamate-gated chloride channel, and also encompasses novel agents identified by such methods. The agent may be an agonist, i.e. it mimics the action of glutamate by activating chloride flux, or an antagonist, i.e. it decreases the glutamate-activated chloride flux. The agent may be nucleic acid, peptide, protein, a non-protein organic molecule, or any other molecule capable of modulating the activity of the glutamate-gated chloride channel.

A method of identifying an agonist comprises applying the putative agonist to a *Xenopus oocyte*, a cell or membrane expressing the lepidopteran glutamate-gated chloride in the presence of chloride ions, and measuring chloride flux, wherein flux of chloride is indicative of an agonist. A method of identifying an antagonist comprises applying glutamate to *Xenopus oocyte* or a cell or membrane expressing the lepidopteran glutamate-gated chloride channel in the presence of chloride ions and measuring chloride flux; applying the putative antagonist and then, for example about one minute, applying glutamate to the cell or membrane and measuring chloride flux; and comparing the chloride flux obtained in the presence of glutamate alone to the flux obtained under similar conditions in the presence of both putative antagonists and glutamate, wherein a decrease in flux of chloride observed in the presence of the putative antagonist relative to the flux observed in the presence of glutamate along is indicative of an antagonist. In a preferred embodiment, chloride flux is measured by voltage clamp electrophysiology. In another preferred embodiment, the cell is an recombinant baculovirus-infected Sf9 cell or a permanently transformed cell line. In another preferred embodiment, the concentrations of agonists, antagonists and GABA are from about 0.1 nM to about 1.0 mM.

Agonists and antagonists against the lepidopteran glutamate-gated chloride channel can also be identified by ligand binding assays. Agonists and antagonists are identified by their ability to displace radiolabeled ligands known to act as agonists or antagonists, respectively. The recombinant glutamate-gated chloride channel, present in an *oocyte*, cell, or membrane, (preferably a membrane) is incubated with radiolabeled ligand and unlabeled candidate agonist or antagonist. After incubation, the incubation mixture is filtered, and radioactivity retained on the filters is measured by methods known in the art, for example liquid scintillation counting. The ability of the candidate compound to inhibit specific binding of the radiolabeled ligand provides a measure of the compound's agonist or antagonist activity. Suitable ligands include glutamate and ivermectin phosphate.

Agents identified by the foregoing methods may be useful as insecticides. Agents identified by the present methods may be assessed for insecticidal activity by in vitro and in vivo methods known in the art.

Another embodiment of the present invention provides a composition comprising a recombinant lepidopteran glutamate-gated chloride channel in a cell membrane. The composition may be a membrane preparation, including a freeze dried membrane preparation, or an intact cell or *oocyte* expressing the functional lepidopteran glutamate-gated chloride channel. The composition is useful, for example, to screen for potential insecticides by functional or specific binding assays. The composition may further comprise appropriate carriers or diluents, including, for example, physiological buffers.

The present invention further provides a kit for identifying agents that modulate the activity of a lepidopteran glutamate-gated chloride channel. The kit contains a first container containing a recombinant lepidopteran glutamate-gated chloride channel in a cell membrane. The membrane may be in the form of a membrane preparation, including a freeze dried membrane preparation, or an insect cell or *oocyte* expressing the functional lepidopteran glutamate-gated chloride channel. The kit of the present invention optionally further comprises glutamate. The compositions and kits of the present invention are useful for identifying insecticides.

All references cited herein are incorporated in their entirety.

The following nonlimiting examples serve to further illustrate the present invention.

EXAMPLE 1

RNA Isolation

*Heliothis virescens* embryo were isolated from eggs just before hatching obtained from Rhone-Poulenc in-house insectary, and *Heliothis virescens* muscles were obtained by dissecting early 5$^{th}$ instar *Heliothis virencens* larva to remove the fat body, but, and central nervous system. Eggs and remaining larva skins were frozen in liquid nitrogen, and ground to powder. Powders were added to lysis buffer, and homogenized before proceeding with manufacturer's instruction for total RNA isolation using Poly(A)Pure™ kit from Ambion. Poly A$^+$ RNA were selected twice by going through a oligo dT column. The RNA recovered from the column was dissolved in diethylpyrocarbonate (DEPC)-treated water. RNA was quantified by spectrophotometry and separated on a denaturing agarose gel to check its integrity before use in RT-PCR and cDNA library construction.

PCR Using Degenerate Primers

Two degenerate oligonucleotides, mw 01 and mw 02, were designed and synthesized from highly conserved regions found in glutamate-gated chloride channel family following the amino acid sequence for *Drosophila melanogaster* GluCl (Cully et al. (1996) J. Biol. Chem. 271:20187), *Caenorhabditis elegans* GluCl-α and *C. elegans* GluCl-β (Cully et al. (1994) Nature 20:371). Primer mw 01 has the sequence 5'-GGATGCC(ATGC)GA(TC)(TC)T(ATGC)TT(TC)TT-3'. (SEQ ID NO.: 1) Primer mw02 has the sequence 5'-TC(ATGC)A(AG)CCA(AG) AA(ATGC)(GC)(AT)(ATGC)ACCC-3'. (SEQ ID NO.:2). The primer mw 01 was located upstream of the transmembrane (TM) domain 1, while downstream primer mw 02 was located within the TM domain 1. the primer mw 02 was used to synthesize first strand cDNA from mRNA isolated from Heliothis embryo using Boehringer Mannheim's 1$^{st}$ Strand cDNA Synthesis Kit for RT-PCR. The cDNA was used as the template for a hot start PCR mix (100 μl) containing: 0.8 mM dNTP's, 2 mM MgCl$_2$, 1.2 pmol/μl degenerate primers and 5U Pfu DNA polymerase (Stratagene). The amplification was performed using 35 cycles of denaturation at 94° C. for 1 min, annealing at 53° C. for 1 min and elongation at 72° C. for 1 min. The denaturation step of the first cycle was 5 min long and the elongation step of the last cycle was 10 min (Perkin Elmer, DNA Thermal Cycler 480) (Sambrook et al., 1989, Molecular Cloning—A laboratory Manual. Cold Spring Harbor Laboratory Press).

PCR generated a 451 base pair (bp) fragment which was cloned into the pCR-Blunt vector (Invitrogen) to produce pE6 and sequenced. The amplified fragment had the following sequence: 5'-GGA TGC CGG ATT TGT TTT TCT CCA ACG AGA AGG AAG GTC ATT TCC ACA AC A TCA TCA TGC CGA ACG TGT ACA TCC GGA TCT TCC CCA ACG GCA ACG TGC T GT ACA GCA TCC GAA TCT CCT TGA CGC TCT CGT GCC CCA TGA ACC TCA AGT TGT ACC CCC TGG ATA AGC AGA CCT GCT CGC TCA GGA TGG CTA GTT ATG GT T GGA CCA CAG ACG ACT TAG TGT TCC TAT GGA AGG AAG GCG ACC CGG TGC AGG TGG TGA AGA ACT TAC ACC TGC CTC GGT TCA CGC TGG AGA AGT TCC TCA CTG ACT ACT GCA ACA GTA AGA CTA ATA CCG GTG AAT ACA GTT GCC TGA AGG TAG ACT TGC TCT TCA AAC GCG AGT TCA GTT ACT ACC TGA TCC AGA TCT ACA TTC CGT GCT GCA TGC TGG TCA TCG TGT CCT GGG TCA CCT TTT GGC TCG A-3' (SEQ ID NO: 3).

Rapid Amplification of cDNA Ends (RACE-PCR)

RACE reactions (Frohman et al. 1988 Proc. Natl. Acad. Sci. USA 85:8998), used to obtain the 5' and 3' ends of the *Heliothis virescens* mRNA, was performed using synthesized double stranded cDNA as the template. Two microgram of polyA mRNA from either *Heliothis virescens* embryo or muscle were used to synthesize cDNA with a Marathon cDNA amplification kit (CLONTECH) following the manufacturer's instructions. Specific primer mw03, derived from 451 bp fragment and having the sequence 5'-CCTGCACCGGGTCGCCTTCCTTCC-3', (SEQ ID NO:4) along with the adapter primer (AP1, 5'-CCATCCTAATACGACTCACTATAGGGC-3') (SEQ ID NO: 5) provided in the kit were used for the amplification of 5' cDNA end. Primer mw04, derived from 451 bp fragment and having the sequence 5'-TACAGCATCCGAA TCTCCTTGACGC, (SEQ ID NO: 6) along with the primer AP1 were used for the amplification of 3' cDNA end. The PCR reactions were carried under the same conditions as in above section except using "touchdown PCR", which was performed using 5 cycles of denaturation at 94° C. for 30 sec, annealing and elongation at 72° C. for 4 min; 5 cycles of denaturation at 94° C. for 30 sec, annealing and elongation at 70° C. for 4 min; and 25 cycles of denaturation at 94° C. for 30 sec, annealing and elongation at 70° C. for 4 min; and 25 cycles of denaturation at 94° C. for 20 sec, annealing and elongation at 68° C. for 4 min. The denaturation step of the first cycle was 1 min at 94° C. One tenth of the PCR reaction (10 μl) was separated on a 1.2% agarose gel containing 1 μg/ml ethidium bromide. The amplified fragments from both 5'RACE and 3'RACE were cloned into pCR2.1 vector (Invitrogen) to produce plasmids designated p5'E4 and p3'm5, respectively. Fragment in p5'E4 has the following sequence: CGC TGA GCA TTG CGA ACT ACG CCT TCA ACA TTG TTT TTT TAA ACA AGC ACC GTT TTT TAA TTT TAA AAG CTC TCA TTA AAG GTT TTA TTT GAA GGA AAG TTG TGA CAG CAA CCG GAG TCG TTT AGA ATG GGA CTT TGT TGA GTC AGA GGA TGG ACA TCC CGC GGC CAT CAT GCG CCC TCG TAT TGG TGT TGT TAT TTG TCA CCC ATC TCT CAG AAT GCA TGA ACG GTG GGA AGA TCA ACT TCC GAG AGA AGG AGA AGC AGA TCC TGG ATC AGA TCC TGG GCC CCG GGA GGT ACG ACG CCA GGA TCA GAC CCT CGG GGA TCA ACG GCA CCG ATG GGC CAG CGG TAG TGA GCG TCA ATA TAT TTG TCC GAA GTA TAT CAA AGA TCG ATG ATG TCA CAA TGG AAT ACT CCG TAC AGT TAA CGT TTC GGG AAC AAT GGT TAG ATG AAC GGC TCA AAT TCA ATA ATC TTG GAG GTC GCC TCA AAT ACC TGA CGC TTA CCG AAG CCA ACA GAG TCT GGA TGC CTG ATC TAT TCT TCT CCA ACG AGA AGG AAG GTC ATT TCC ACA ACA TCA TCA TGC CGA ACG TGT ACA TCC GAA TCT TCC CCA ACG GCA ACG TGC TGT ACA GCA TCC GAA TCT CCC TGA CGC TCT CGT GCC CCA TGA ACC TCA AGT TGT ACC CCC TGG ATA AGC AGA CCT GCT CGC TCA GGA TGG CTA GTT ATG GTT GGA CCA CAG ACG ACT TAG TGT TCC TAT GGA AGG AAG GCG ACC CGG TGC AGG. (SEQ ID NO: 7)

Fragment in p3'm5 has the following sequence: 5'-CGC TCT CGT GCC CCA TGA ACC TCA AGT TGT ACC CCC TGG ATA AGC AGA CCT GCT CGC TCA GGA TGG CTA GTT ATG GTT GGA CCA CAG ACG ACT TAG TGT TCC TAT GGA AGG AAG GCG ACC CGG TCG AGG TGG TGA AAA ACT TAC ACC TGC CTC GGT TCA CGC TGG AGA AGT TCC TCA CTG ACT ACT CGA ACA GTA AGA CTA ATA CCG GTG AAT ACA GTT GCC TGA AGG TAG ACC TGC TCT TCA AAC GCG AGC TCA GTT ACT ACC TGA TCC AGA TCT ACT TTC CGT GCT GCA TGC TGG TCA TCG TGT CCT GGG TGT CCT TCT GGC TGG ACC AGG GAG CTG TGC CTG CGA GGG TCT CAC TAG GAG TGA CGA CTT TAC TTA CAA TGG CGA CCC AGT CGT CAG GCA TCA ACG CGT CCC TAC CAC CGG TGT CCT ACA CGA AAG CCA TTG ATG TCT GGA CTG GTG TAT GTC TCA CAT TCG TAT TCG GAG CGC TAC TAG AGT TCG CGC TCG TCA ACT ATG CGT CT C GCT CTG ACA TGC ACC GAG AGA ACA TGA AGA AAG CGA GAC GGG AGA TGG AA G CAG CCA GCA TGG ATG CTG CCT CAG ATC TCC TTG ATA CAG ATA GCA ACA CCA CC TTT GCT ATG AAA CCC TTG GTG CGC GGC GGC GTG GTG GAA TCC AAG ATG CGG CAG TGC GAG ATC CAC ATC ACC CCG CCG CGG AAG AAC TGC TGC CGC CTG TGG ATG TCC AAG TTC CCC ACG CGC TCC AAG AGG ATAGAC GTCATC TCC AGG ATC ACC TTC CCA CTT GTG TTC GCT CTG TTT AAC CTG GCT TAC <u>TGA</u> ATG AAG CAG AGA AAC TCC TCC TTT GCG CAC AGA AAT CCT GAA GAG ACT GAA CAA CGA AGT TTC CTA ACC ACA ATC ATT GCT ATG ATT ATA CCG AGA ATT TAT TTT ATA CTA ATT GTT GTG ACC ACA CGG TTT TAA GCT AGC TTG GAT CCA CGC GGT GTT AAT ATT TGT TGA TCG CTT AGA ATA AAT AAA TAT GCT TTG TTG AAA AAA AAA AAA AAA AAA AAA AAA AAA AAA AAA-3' (SEQ ID NO: 8).

Generation of Full-Length cDNA by PCR:

5' and 3'-end gene specific primers (GSP) were designed based on the sequence obtained from previous 5'- and 3'-RACE products. 5' GSP1 has the following sequences: 5'-GCTGAGCATTGCGAACTACGCTTCAAC3', (SEQ ID NO:9) and 3' GSP2 has the following sequences:5'-TAACACCGCGTGGATCCAAGCTACG3' (SEQ ID NO:10). Full-length cDNAs from both Heliothis embryo and muscle were generated using 5' GSP1 and 3' GSP2 in a long distance PCR reaction which used following cycle condition: 1 cycle of denaturation at 94° C. for 1 min, and 25 cycles of denaturation at 94° C. for 30sec and annealing and extension at 72° C. for 5 min using pfu as polymerase. The amplified fragments from both Heliothis embryo and muscle were cloned into pCR2.1-TOPO vector (Invitrogen) to generate plasmids HEG3E(4)-2 and HEGM(1)-3.

HEG3E(4)-2 has the following sequences (SEQ ID NO:11):

1 GtGAGCATTG CGAACTACGC CTTCAACATT GTTTCTTTAA ACAAACACCG TTTTTTAATT

61 TTAATAGCAC TCATTAAAGG TTTTATTTGA AGGAAAGTTG TGACAGCAAC CGGAGTCGTT

121 TAGAATGGGA CTTTGTTGAG TCGGAGGATG GACATCCCGC GGCCATCATG CGCCCTCGTA

181 TTGGTGTTGT TATTTGTCAC CCATCTCTCA GAATGCATGA ACGGTGGGAA GATCAACTTT

241 CGAGAGAAGG AGAAGCAGAT CCTGGATCAG ATCCTGGGCC CCGGGAGGTA CGACGCCAGG

301 ATCAGACCCT CGGGGATCAA CGGCACTGAT GGGCCAGCGG TAGTGAGCGT CAATATATTT

361 GTCCGAAGTA TATCAAAGAT CGATGACGTC ACAATGGAAT ACTCCGTACA ATTAACGTTT

421 CGGGAACAAT GGTTAGATGA ACGGCTCAAA TTCAATAATC TTGGAGGTCG CCTCAAATAC

481 CTGACACTGA CTGAAGCCAA CAGAGTCTGG ATGCCTGATC TATTCTTCTC CAACGAGAAG

541 GAAGGTCATT TCCACAACAT CATCATGCCG AACGTGTACA TCCGAATCTT CCCCAACGGC

601 AACGTGCTGT ACAGCATCCG AATCTCCCTG ACGCTCTCGT GCCCCATGAA CCTCAAGTTG

661 TACCCCCTGG ATAAGCAGAC CTGCTCGCTC AGGATGGCTA GTTATGGTTG GACCACAGAC

721 GACTTAGTGT TCCTATGGAA GGAAGGCGAC CCGGTGCAGG TGGTGAAAAA CTTACACCTG

781 CCTCGGTTCA CGCTGGAGAA GTTCCTCACT GACTACTGCA ACAGTAAGAC TAATACCGGT

841 GAATACAGTT GCCTGAAGGT AGACCTGCTC TTCAAACGCG AGTTCAGTTA CTACCTGATC

901 CAGATCTACA TTCCGTGCTG CATGCTGGTC ATCGTGTCCT GGGTGTCCTT CTGGCTGGAC

961 CAGGGAGCTG TGCCTGCAG GGTCTCACTA GGAGTGACGA CTTTACTTAC AATGGCGACC

1021 CAGTCGTCAG GCATCAACGC GTCCCTACCA CCGGTGTCCT ACACGAAAGC CATTGATGTC

1081 TGGACTGGGT TATGTCTCAC ATTCGTATTC GGAGCGCTAC TAGAGTTTGC GCTCGTCAAC

1141 TATGCGTCTC GCTCTGACAT GCACCGAGAG AACATGAAGA AAGCGAGACG GGAGATGGAA

1201 GCAGCCAGCA TGGATGCTGC CTCAGATCTC CTTGATACAG ATAGCAACAC CACCTTTGCT

1261 ATGAAACCCT TGGTGCGCGG CGGCGTG-GTG GAATCCAAGA TGCGGCAGTG CGAGATCCAC

1321 ATCACCCCGC CGCGGAAGAA CTGCTGCCGC CTGTGGATGT CCAAGTTCCC CACGCGCTCC

1381 AAGAGGATAG ACGTCATCTC CAGGATCACC TTCCCACTTG TGTTCGCTCT GTTTAACCTG

1441 GCTTACTGAA TGAAGCAGAG AAACTCCTCC TTTGCGCACA GAAATCCTGA AGAGACTGAA

1501 CAACGAAGTT TCCTAACCAC AATCATTGCT ATGATTATAC CGAGAATTTA TTTTATACTA

1561 ATTGTTGTGA CCACACGGTT TAAACGTAGC TTGGATCCAC GCGGTGTTA

HEGM(1)-3 has the following sequence (SEQ ID NO:12):

1 AGGTGCGGAC GTCTGCACTT GCGAATCGAA GTGATAGAAA ATAGTTCGAT GAATACGGGA

61 GTTTGAGTGG AGTGATTTAT AATTCGGAGG ATGGACATCC CGCGGCCATC ATGCGCCCTC

121 GTATTGGTGT TGTTATTTGT CACCCATCTC TCAGAATGCA TGAACGGTGG GAAGATCAAC

181 TTTCGAGAGA AGGAGAAGCA GATCCTGGAT CAGATCCTGG GCCCCGGGAG GTACGACGCC

241 AGGATCAGAC CCTGCGGGAT CAACGGCACT GGCTATGCGC CAACGTTAGT CCATGTCAAC

301 ATGTATCTAC GGTCCATCAG CCCCCTAGAT GATTACAAAA TGGAATACTC CGTACAATTA

361 ACGTTTCGGG AACAATGGTT AGATGAACGG CTCAAATTCA ATAATCTTGG AGGTCGCCTC

421 AAATACCTGA CACTGACTGA AGCCAACAGA GTCTGGATGC CTGATCTATT CTTCTCCAAC

481 GAGAAGGAAG GTCATTTCCA CAACATCATC ATGCCGAACG TGTACATCCG GATCTTCCCC

541 AACGGCAACG TGCTGTACAG CATCCGAATC TCCCTGACGC TCTCGTGCCC CATGAACCTC

601 AAGTTGTACC CCTGGATAA GCAGACCTGC TCGCTCAGGA TGGCTAGTTA TGGTTGGACC

661 ACAGACGACT TAGTGTTCCT ATGGAAGGAA CGCGACCCGG TGCAGGTGGT GAAAAACTTA

721 CACCTGCCTC GGTTCACGCT GGAGAAGTTC CTCACTGACT ACTGCAACAG TAAGACTAAT

781 ACCGGTGAAT ACAGTTGCCT GAAGGTAGAC CTGCTCTTCA AACGCGAGTT CAGTTACTAC

841 CTGATCCAGA TCTACATTCC GTGCTGCATG CTGGTCATCG TGTCCTGGGT GTCCTTCTGG

901 CTGGACCAGG GAGCTGTGCC TGCGAGGGTC TCACTAGGAG TGACGACTTT ACTTACAATG

961 GCGACCCAGT CGTCAGGCAT CAACGCGTCC CTACCACCGG TGTCCTACAC GAAAGCCATT

1021 GATGTCTGGA CTGGGTTATG TCTCACATTC GTATTCGGAG CGCTACTAGA CTTTGCGCTC

1081 GTCAACTATG CGTCTCGCTC TGACATGCAC CGAGAGAACA TGAACAAAGC GAGACGGGAG

1141 ATGGAAGCAG CCAGCATGGA TGCTGCCTCA GATCTCCTTG ATACAGATAG CAACACCAC

1201 TTTGCTATGA AACCCTTGGT GCGCGGCGGC GTGGTGGAAT CCAAGATGCG GCAGTGCGAG

1261 ATCCACATCA CCCCGCCGCG GAAGAACTGC TGCCGCCTGT GGATGTCCAA GTTCCCCACG

1321 CGCTCCAAGA GGATAGACGT CATCTCCAGG ATCACCTTCC CACTTGTGTT CGCTCTGTTT

1381 AACCTGGCTT ACTGTTGGGG GGGCAA-GAGG GGGCGGTGG CTGCTACCAT GTCTTGCAGG

1441 AGCGATGAGA CTATTAATGC TATTTATAAG CTGATACAGA ATGAAGCAGA GAAACTCCTC

1501 CTTTGCGCAC AGAAATCCTG AAGAGACTGA ACAACGAAGT TCCCTAACCA CAATCATTGC

1561 TATGATTATA CCGAGAATTT ATTTTATACT AATTGTTGTG ACCACACGGT TTTAAGCTAG

1621 CTTGGATCCA CGCGGTGTTA

EXAMPLE 2

Isolation of full-length clone by screening of cDNA library:

Compared to the glutamate-gated chloride channel clones from Drosophila and C. elegans, clone HEG3(E)-2 has a stop codon within the M4 transmembrane domain, whereas clone HEGM(1)-3 has an unusual long 3' sequence after the M4 transmembrane domain. It is unclear whether these two clones resulted from different RNA splicing or due to the errors introduced by PCR polymerase during the RACE reaction. cDNA libraries of *Heliothis virescens* embryo and muscle were constructed using 7.5 μg of each of isolated polyA mRNA with Stratagene's cDNA Synthesis kit.

The cDNAs were made according to the manufacturer's instructions and then cloned into the lambda ZAP expression cloning vector and packaged with Gigapack III Gold packaging system (Stratagene) following the manufacturer's instructions. Thus two non-amplified libraries of 5×10⁵ recombinants were made and then amplified.

Clone HEG3(E)-2 insert was cut out from its vector by SacI enzyme, and was labeled with $^{32}$P using Boehringer Mannheim's Random Primed DNA Labeling Kit (CA#1004760). Part of the amplified *Heliothis virescens* embryo library was plated out on 10 large 150-mm NZY agar plate at 50,000 pfu/plate. Phage particles were transferred to nitrocellulose membranes. Membranes were denatured in a 1.5 M NaCl and 0.5 M NaOH denaturation solution for 5 minutes, neutralized in a 1.5 M NaCl and 0.5 M Tris-Cl (pH 8.0) neutralization solution for 5 minutes and rinsed in a 0.2 Tris-Cl (pH 7.5 ) and 2×SSC buffer for 2 minute. DNA was crosslinked to the membranes using the Stratalinker UV crosslinker (CL-100 Ultraviolet Crosslinker, UVP). Prehybridization was performed in a 50 ml solutions containing:25 ml of formamide, 12.5 ml of 20×SSC, 0.5 ml of 10% SDS and 5 ml of Derhardt solution at 42C. for 3–4 hours. Labeled probes were added to the prehybridization solution at 1.84×10⁵ dpm/ml$^{32}$P and hybridization was continued at 42° C. for 24 hours. Membranes were washed twice for 15 minutes in low stringency conditions (2×SSC/0.1% SDS, room temperature), twice for 15 minutes in high stringency conditions (0.2×SSC/0.1%SDS,42C.), and once for 15 minutes in higher stringency conditions (0.1×SSC/0.1% SDS, 42C.). Ten positive clones were identified and plaques were purified, and secondary and tertiary screenings were performed using the same primer with positive clones to make sure that each positive plaque was very well separated. The phagemids containing the inserts were excised following the manufacturer's instruction (Stratagene). Two clones which have the same full-length sequences of glutamate-gated chloride channels, were designated HEGE2. The following DNA sequence (SEQ ID NO:13) for clone HEGE2 was determined:

1 ACCAGGCGAA CTACGCCTTC AACATTGTTT TTTTAAACAA ACACCGTTTT TTAATTTTAA
61 TAGCTCTCAT TAAAGGTTTT ATTTGAAGGA AACTTGTGAC AGCAACCGGA GTCGTTTAGA
121 ATGGGACTTT GTTGAGTCGG AGGATGGACA TCCCGCGGCC ATCATGCGCC CTCGTATTGG
181 TGTTGTTATT TGTCACCCAT CTCTCAGAAT GCATGAACGG TGGGAAGATC AACTTTCGAG
241 AGAAGGAGAA GCAGATCCTG GATCAGATCC TGGGCCCCGG GAGGTACGAC GCCAGGATCA
301 GACCCTCGGG GATCAACGGC ACTGATGGGC CAGCGGTAGT GAGCGTCAAT ATATTTGTCC
361 GAAGTATATC AAAGATCGAT GACGTCACAA TGGAATACTC CGTACAGTTA ACTTTTCGGG
421 AACAATGGTT AGATGAACGG CTCAAATTCA ATAATCTTGG AGGTCGCCTC AAATACCTGA
481 CACTGACCGA AGCCAACAGA GTCTGGATGC CTGATCTATT CTTCTCCAAC GAGAAGGAAG
541 GTCATTTCCA CAACATCATC ATGCCGAACG TGRACATCCG GATCTTCCCC AACGGCAACG
601 TGCTGTACAG CATCCGAATC TCCTTGACGC TCTCGTGCCC CATGAACCTC AAGTTGTACC
661 CCCTGGATAA GCAGACCTGC TCGCTCAGGA TGGCTAGTTA TGGTTGGACC ACAGACGACT
721 TAGTGTTCCT ATGGAAGGAA GGCGACCCGG TGCAGGTGGT GAANAACTTA CACCTGCCTC
781 GGTTCACGCT GGAGAAGTTC CTCACTGACT ACTGCAACAG TAAGACTAAT ACCGGTGAAT
841 ACAGTTGCCT GAAGGTAGAC TTGCTCTTCA AACGCGAGTT CAGTTACTAC CTGATCCAGA
901 TCTACATTCC GTGCTGCATG CTGGTCATCG TGTCCTGGGT GTCCTTCTGG CTGGACCAGG
961 GAGCTGTGCC TGCGAGGGTC TCACTAGGAG TGACGACTTT ACTTACAATG GCGACCCAGT
1021 CGTCAGGCAT CAACGCGTCC CTACCACCGG TGTCCTACAC GAAAGCCATT GACGTCTGGA
1081 CTGGTGTATG TCTCACATTC GTATTCGGAG CGCTACTAGA GTTCGCGCTC GTCAACTATG
1141 CGTCTCGCTC TGACATGCAC CGAGAGAACA TGAAGAAAGC GAGACGGGAG ATGGAAGCAG
1201 CCAGCATGGA TGCTGCCTCA GATCTCCTAG ACACAGATAG CAACACCACC TTTGCTATGA
1261 AACCCTTGGT GCGCGGCGGC GTGGTGGAAT CCAAGATGCG GCAGTGCGAG ATCCACATCA
1321 CCCCGCCGCG GAAGAACTGC TGCCGCTGT GGATGTCCAA GTTCCCCACG CGCTCCAAGA
1381 GGATAGACGT CATCTCCAGG ATCACCTTCC CACTTGTGTT CGCTCTGTTT AACCTGGCTT
1441 ACTGGTCGAC GTACCTGTTC CGCGACGAGG ACGAGGAGAA GTGATTCTCC GAGTCCCTGG
1501 AGAGGGGCGT GGGGCCGCGC GTGCAGCTGG TGGCGGCCGT CGTGATGCCC TACGTGCTGT
1561 TCGTGGTGGC GTACTCGCTG TGCTTCCGCG CGCGCGCCCC GCCCCCTTCG CCCCCGCCCG
1621 CGCCCGCGCC CGCGCCCTCG CCCGCACCCT CCCGCCGCAG CGCGCGCGCA CGCACACAAG
1681 CACACCCACC TAGCCCGCTC TAGCGAACTC ACCCCATTCA TTATCGTGAC ATATTATATT
1741 ATCGTGTATT TTAATCGACG TCTTCCTCGT GGCAGCGTTA TTCCCACTCA GTATTCGATG
1801 GCGTTAGTGT AATTAGTAAA GCTCAAGTGT CTATTTGTAT ATATATGTGA CCCCCGTGCC
1861 AGTTTAGACC AAGCCTCCGT TTTTAAATTG AAGCAGTTCG AGAAAAACGG TAAAAATAGA
1921 CTCAATTTTG ATTGGTCATC TAAACAGCAG AACTTTTATT CGGCACTTAT AAAGTCCTCA
1981 ATTATTTGTG TACAAAAATA AATATTTTAC TTTCCGAGAA TTAAAAATTT TCGATAATTT
2041 TACCAATGAT ATGACTCCTT GTATGGATTC GTATGTAATG TAAACCTAGG TTAAGATATA
2101 AGAGGAATCC CAGAGGTTCC CGCATATTAC TTTAGCCTTT AAAGTAAGGT AAATAAGGAC
2161 TAGAATGGCA CTAATGTGTA CTGGAAGTGG GGTATTATTT ATTAGTTTTC ACTCTACAGT
2221 ACGTGAACTG GACTAGATCT ACTAGCAAAT AGAGTTGATC AATTTTCATG TCGAAATGTT
2281 CACAGATATT GTATAAACCG CTGGAGGTAA ACAGCTATCA ACAATGTAAC ACCAAATACC
2341 ATCAGAATCA AGCAAAACCA TGGAAATTTT GCTGGTCGAA AAGTTGTAAC TGTTTATCTA
2401 TGGCAGGTAT AATTGGCCTA GTAATGTATC GTGTAGTATC ATTTACAACA CATATTAACT
2461 ATTAACCACA TTATGTGAAA GAAGGAATTT ATAAAAAAAA CCTTATTAAA TATATATTAG

2521 ATAAGTATTA TTAATTGGAT ATTCTCTTGC TGGGGATTTT AATATGAATC TTACCTTTAA
2581 ATAAGTTTGA TCTCACTAGA CGTTGCAAAT GGATACCCCA AATACCTTTT CCGCATTAAA
2641 AGGTATTATT TTAACAAATG TATTCTTCCC CGTCAATGTT TTAAGACTAC GTATCTACAT
2701 AAAATGATGT ATTGTTCATA CAATACTATT TCAAAATGCA AGAACAACGT AAAGTGCATT
2761 TCATTGATGT TTGTGTATGT ACATCACATT AGTATTTTAC CCAAAAATAC TGATATTAAA
2821 ATTCCCAGTA AGATTCGTAG GTAAATGGTA AACGTGTAAA TAGTTGGGCC TACAACTTTC
2881 TACACCTGTG TCGCTCAGTG TACAGTTACC TATATTTAAT ATTACAATTA TATCATTATT
2941 AACGAATGAT AAGATTTTAT TAACATTAAT TTCTCTGTCT GAACGTATCA CTGTAAATAT
3001 TACTAAATGT TTCCTAATTA CATTATTCAT ACATATATTA TCATCCCTTG AGCTATAGTT
3061 GCAAAGTATT CCAAAACCAC AATGAAAATA AAATTTCAAT TTACTTCACG ATCACCAAAT
3121 TGTGAAAACC TGGTTGTTCT GAATTCATTT AACAATTAGT TTTTACTTTG AATCCATGGC
3181 TCAAGGGACA TCCTAAGGAT ATTCATTGAA ATCTATTTAG AATCTCGTGT ATGTATCATG
3241 ACACCTTCAA ATAAAATATC ACTAATGCTG TGTTCGGCTA TTAGATACAA TAAGTCGTAC
3301 ATATTAACGT AAGCACATTC GTTTTTATTA TGCGGCGGAG AGAACGCATC TGTTTCTATA
3361 ACGAAAGGGT GGCCATTATC GGCTATATCA TCTTGCTTGG TCTGTATAAA AATAAGAGTC
3421 AAAGACTCGG GGGAAACCCC TATATGTATA CTATCATAAC CGTTATCCTT ATTTTGACAA
3481 AGCTCTGGGA AACGAAATAG CATTTTGTTT CAATTACACA ATTCTTGCTC ATTTTCTCT
3541 TCCGCCTTTT ATTTGAATTT AGGTGTTGCC CACTGTGCGC AATACTCTAA TGGCTTAGAA
3601 TTATCCTTAA TATATATTCT CGGGCTGTGA CGAGGTGTAG CATCTGCATT ATTATATTAA
3661 TGTCATTTCG TTTGCCATTC GTTGTATGTA AGGAAATATT AGCCTATGTC CAACGCTCAA
3721 AATCTCATAG ACGTATTAGG CACACATAAG TGTACCTTTT CGTATGTATG TAAATTATTG
3781 GAGACTCAAT GTCTTAGTTG GTGCTATATA TACTACGATC CGAGGAGAAT GTACCCAGTA
3841 GTTTACTCAT ACATAACGCC ACTGATATCT TGTGGAGGAA ATATTATCTG CGAGACAAGT
3901 AGACATTAGT TAAGTTTACA TATTTACAAT AAATGTTTCC ATTATTAGGA TATAACATAT
3961 GAATGTGTTA CTGTTGAAAG CAGCTTCTCA AGGTACCACC AGTAATTCGG AGATACTTGT
4021 AGGATTTGCA TTCGATAAAC AACTTATACT AAAACGAAGA TTTGACTGAA TCTAAACCGC
4081 AAATACTGTG GTCAAAATTA TTAAACACTT TCAATACATG TTGTACGCAT GTTTCTGTAA
4141 TTTCACATTT AATTGTAAAG TCAATTAAAT CACTGTATAA TAATACATTT TCAACATATC
4201 TCTCACTGTT AAGATTTCGG TTGGTCCAAC GACAGAATCA AATCGCAACG TAATGATGAT
4261 CCGGGCAAAA CTAACAACTA GATAGATCTC TTAAATGATT ACGTTGAAGT GGAAGAGGTG
4321 ATGTATGAAG GAAGGTAGGA TTAAGTAACA CTGTATAATA TATTGACCAT AATTACGATT
4381 TTAGAAGTCA TAATGGACGG TTTACCTCTT AAGATTATAC AGTAAAGGTA GATAGTTTCA
4441 TTCGTAAGCT ATGTTGTACT CGATTGGTAT GACATAACTA ATGACTGAGC TTTGTCATCT
4501 ACTACAACCC GAGGGCGAAT ACCTCCTTCT TCTACCATTC CCATTTAATT ATAAAGAAAC
4561 ATTGTAAAAA ATGATTTAAT AAAATATCCC AAATATCTTA AAACAAAAAA AAAAAAAAAA
4621 A

Sequencing indicated that HEGE2 encoded a full length Heliothis virescens glutamate-gated chloride channel clone directionally cloned into the EcoRI and XhoI sites of phagemid pBluescript SK (+/−). The coding sequence starts at 144 bp and ends at 1484 bp, and encodes a polypeptide of 444 amino acids having the predicted sequence (SEQ ID NO:14): MDIPRPSCALVLLFVTHLSECMNGGKIN-FREKEKQILDQILGPGRYDARIRPSGINGTDGP AVVS-VNIFVRSISKIDDVTMEYSVQLT-FREQWLDERLKFNNLGGRLKYLTLTEANRVW MPDLFFSNEKEGHFHNIIMPNVYIRIFP-NGNVLYSIRISLTLSCPMNLKLYPLDKQTCSLR MASYGWTTDDLVFLWKEGDPVQVVKN-LHLPRFTLEKFLTDYCNSKTNTGEYSCLKVD LLFKREFSYYLIQIYIPCCMLVIVSWVS-FWLDQGAVPARVLLGVTTLLTMATQSSGINAS LPPV-SYTKAIDVWTGVCLTFVFGALLESRFVN-YASRDMNHRENMKKARREMEAASMD AASDLLDTDSNTTFAMKPLVRGGVVESK-MRQCEIHITPPRKNCCRLWMSKFPTRSKRID VISRIT-FPLVFALFNLAYWSTYLFRDEDEEK BLAST search BLAST search (http://www.ncbi.nlm.gov) and amino acid sequence comparison were used to identify glutamate-gated chloride channel-like fragments from the PCR products amplified with degenerate primers, the PCR products obtained from RACE and clones screened from embryo cDNA library. BLAST was also used to determine the orientation and the position of the amplified products compared to the entire cDNA sequence.

EXAMPLE 3

Expression of Nucleic Acid Encoding Lepidopteran Glutamate-gated Chloride Channel in Xenopus Oocytes:

Messenger RNA was produced from the cDNA template of HEGE2 by in vitro transcription with the Ambion mMESSAGE mMACHINE IN VITRO TRANSCRIPTION KIT (Ambion, Inc.). The mRNA was injected into oocytes by the following procedure.

Frogs were anesthetized in a 2 gram/liter solution of 3-amino benzoic acid ethyl ester for thirty minutes, after which oocytes were surgically removed from the abdominal cavity. Follicles were digested by collagenase treatment under sterile conditions by standard methods. Oocytes were injected with 50 nl of 1 $\mu g/\mu l$ mRNA by glass electrodes.

After a 24 hr incubation, two-electrode voltage clamp recordings were made. Recordings were made using a Dagan, TEV200 voltage clamp interfaced with a MacLab4 data acquisition system running the MacLab Chart data acquisition/analysis software. Oocytes were positioned under a dissection scope under constant perfusion with frog saline (96 mM of NaCl, 2 mM of KCl, 1 mM of $MgCl_2$, 1.8 mM of $CaCl_2$ and 10 mM of HEPES, pH 7.5) using a Razel syringe perfusion pump. Model A99-FY at 93.9 cc/hr. Glass electrodes (A–M Systems, Inc. 1.5 mm×0.86 mm) were filled with 3 M KCl and resistance (a function of the diameter of the channel opening) was measured to be between 0.7 and 1.5 mega ohms. Both electrodes were inserted into the oocyte at opposite sides, the resting potential was recorded and the voltage clamp turned on. Oocytes were held at a resting potential at −80 mV. Control responses of glutamate were obtained by stopping the perfusion of saline and perfusing with a known concentration of glutamate in frog saline. The average of several glutamate applications were taken as the maximal chloride current for that particular glutamate dose. The effect of 100 micromolar glutamate on the lepidopteran glutamate-gated chloride channel expressed in Xenopus oocytes is depicted in FIG. 1. Glutamate application is indicated by the arrow marked "on". The data in FIG. 1 indicate that 100 uM glutamate activate a membrane current in Xenopus oocytes injected with 50 ng of HEGE2 mRNA. This example demonstrates that the expression of mRNA corresponding to the cDNA in HEGE2 results in a functional glutamate gated chloride channel in oocytes. One micromolar of Ivermectin phosphate also slowly and irreversibly activated current in oocytes.

We claim:

1. An isolated nucleic acid encoding a lepidopteran glutamate-gated chloride channel having the amino acid sequence of SEQ ID NO: 14.

2. The isolated nucleic acid of claim 1 wherein the nucleic acid is DNA or RNA.

3. The isolated nucleic acid of claim 1 wherein the nucleic acid comprises the nucleotide sequence of SEQ ID NO: 13.

4. The isolated nucleic acid of claim 1 wherein the nucleic acid comprises nucleotides 144 through 1484 of SEQ ID NO: 13.

5. An isolated nucleic acid having at least 90% sequence identity to nucleotides 144 to 1484 of SEQ ID NO: 13 wherein said nucleic acid encodes a lepidopteran glutamate-gated chloride channel.

6. The isolated nucleic acid of claim 5 wherein said nucleic acid has at least 95% sequence identity to nucleotides 144 to 1884 of SEQ ID NO: 13.

7. A vector comprising an isolated nucleic acid encoding a lepidopteran glutamate-gated chloride channel having the amino acid sequence of SEQ ID NO: 14.

8. The vector of claim 7 further comprising a promoter operably linked to the isolated nucleic acid.

9. A host cell comprising the vector of claim 7.

10. A host cell comprising the vector of claim 8.

11. A host cell expressing a recombinant lepidopteran glutamate-gated chloride channel having the amino acid sequence of SEQ ID NO: 14.

12. A membrane preparation comprising a recombinant lepidopteran glutamate-gated chloride channel having the amino acid sequence of SEQ ID NO: 14.

13. A method of making a recombinant lepidopteran glutamate-gated chloride channel comprising introducing a nucleic acid encoding a lepidopteran glutamate-gated chloride channel having the amino acid sequence of SEQ ID NO: 14 into a host cell and culturing the host cell under conditions suitable for expressing the nucleic acid.

14. The method of claim 13 wherein the host cell is an insect cell.

15. An amphibian oocyte comprising an isolated nucleic acid encoding a lepidopteran glutamate-gated chloride channel having the amino sequence of SEQ ID NO: 14.

16. An amphibian oocyte expressing a lepidopteran glutamate-gated chloride channel having the amino acid sequence of SEQ ID NO: 14.

17. The oocyte of claim 16 which is a Xenopus oocyte.

* * * * *

UNITED STATES PATENT AND TRADEMARK OFFICE
CERTIFICATE OF CORRECTION

PATENT NO. : 6,329,174 B1
DATED : December 11, 2001
INVENTOR(S) : Wang et al.

It is certified that error appears in the above-identified patent and that said Letters Patent is hereby corrected as shown below:

Title page, Item [54] and Column 1, line 1,
Title, "LEPIDOTERAN" should read -- LEPIDOPTERAN --

Column 1,
Line 57, "*occyte*" should read -- *oocyte* --

Column 2,
Line 6, "channels" should read -- channel --
Line 32, "lepidopiteran" should read -- lepidopteran --

Column 3,
Line 53, "procaryotic" should read -- prokaryotic --

Column 4,
Line 23, "baculovbirus" should read -- baculovirus --
Line 28, "homoogous" should read -- homologous --
Lines 37-38, "lepidopterant" should read -- lepidopteran --
Line 48, "recombinant" should read -- a recombinant --

Column 5,
Line 56, "about" should read -- after about --
Line 64, "along" should read -- alone --

Column 6,
Line 58, "*virencens*" should read -- *virescens* --
Line 59, "but," should read -- gut, --
Line 65, "a" should read -- an --

Column 7,
Line 13, "(SEQ ID NO.:1)" should read -- (SEQ ID NO:1) --
Line 15, "(SEQ ID NO.:2)" should read -- (SEQ ID NO:2) --
Line 23, "Pfu" should read -- *Pfu* --

Column 8,
Lines 15 and 41, "p3´m5" should read -- p3´M5 --

Column 9,
Line 18, "30sec" should read -- 30 sec --
Line 19, "pfu" should read -- *Pfu* --

UNITED STATES PATENT AND TRADEMARK OFFICE
CERTIFICATE OF CORRECTION

PATENT NO. : 6,329,174 B1
DATED : December 11, 2001
INVENTOR(S) : Wang et al.

It is certified that error appears in the above-identified patent and that said Letters Patent is hereby corrected as shown below:

Column 9 (cont'd),
Line 23, "sequences" should read -- sequence --
Line 24, "GtGAGCATTC" should read -- GTGAGCATTC --

Column 11,
Line 4, "unusual" should read -- unusually --
Line 27, "minute" should read -- minutes --
Line 29, "solutions" should read -- solution --
Line 29, "containing:25" should read -- containing: 25 --
Lines 32, 38 and 39, "42C." should read -- 42ºC. --
Line 33, "dpm/ml$^{32}$P" should read -- dpm/ml $^{32}$P --

Column 15,
Line 5, "100 uM" should read -- 100$\mu$m --

Signed and Sealed this

Eleventh Day of November, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide Primer mw 01
<221> NAME/KEY: variation
<222> LOCATION: (8)...(8)
<223> OTHER INFORMATION: n is a, t, g, or c
<221> NAME/KEY: variation
<222> LOCATION: (14)...(14)
<223> OTHER INFORMATION: n is a, t, g, or c

<400> SEQUENCE: 1
ggatgccnga yytnttytt                                            19

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide Primer mw 02
<221> NAME/KEY: variation
<222> LOCATION: (3)...(3)
<223> OTHER INFORMATION: n is a, t, g, or c
<221> NAME/KEY: variation
<222> LOCATION: (12)...(12)
<223> OTHER INFORMATION: n is a, t, g, or c
<221> NAME/KEY: variation
<222> LOCATION: (15)...(15)
<223> OTHER INFORMATION: n is a, t, g, or c

<400> SEQUENCE: 2
tcnarccara answnaccc                                            19

<210> SEQ ID NO 3
<211> LENGTH: 451
<212> TYPE: DNA
<213> ORGANISM: Heliothis virescens

<400> SEQUENCE: 3
ggatgccgga tttgttttc tccaacgaga aggaaggtca tttccacaac atcatcatgc      60
cgaacgtgta catccggatc ttccccaacg gcaacgtgct gtacagcatc cgaatctcct    120
tgacgctctc gtgccccatg aacctcaagt tgtaccccct ggataagcag acctgctcgc    180
tcaggatggc tagttatggt tggaccacag acgacttagt gttcctatgg aaggaaggcg    240
acccggtgca ggtggtgaag aacttacacc tgcctcggtt cacgctggag aagttcctca    300
ctgactactg caacagtaag actaataccg gtgaatacag ttgcctgaag gtagacttgc    360
tcttcaaacg cgagttcagt tactacctga tccagatcta cattccgtgc tgcatgctgg    420
tcatcgtgtc ctgggtcacc ttttggctcg a                                  451

<210> SEQ ID NO 4
<211> LENGTH: 24

<210> SEQ ID NO 4 (implied continuation)
<211> LENGTH: 24
<212> TYPE: DNA
<213> ORGANISM: Artificial Sequence
<220> FEATURE:
<223> OTHER INFORMATION: Oligonucleotide Primer mw 03

<400> SEQUENCE: 4

```
cctgcaccgg gtcgccttcc ttcc                                          24
```

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide Adaptor Primer, AP1

<400> SEQUENCE: 5

```
ccatcctaat acgactcact atagggc                                       27
```

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide Primer mw 04

<400> SEQUENCE: 6

```
tacagcatcc gaatctcctt gacgc                                         25
```

<210> SEQ ID NO 7
<211> LENGTH: 762
<212> TYPE: DNA
<213> ORGANISM: Heliothis virescens

<400> SEQUENCE: 7

```
cgctgagcat tgcgaactac gccttcaaca ttgtttttt  aaacaagcac cgttttttaa    60
ttttaaaagc tctcattaaa ggttttattt gaaggaaagt tgtgacagca accggagtcg   120
tttagaatgg gactttgttg agtcagagga tggacatccc gcggccatca tgcgccctcg   180
tattggtgtt gttatttgtc acccatctct cagaatgcat gaacggtggg aagatcaact   240
tccgagagaa ggagaagcag atcctggatc agatcctggg ccccgggagg tacgacgcca   300
ggatcagacc ctcggggatc aacggcaccg atgggccagc ggtagtgagc gtcaatatat   360
ttgtccgaag tatatcaaag atcgatgatg tcacaatgga atactccgta cagttaacgt   420
tcgggaaca  atggttagat gaacggctca aattcaataa tcttggaggt cgcctcaaat   480
acctgacgct taccgaagcc aacagagtct ggatgcctga tctattcttc tccaacgaga   540
aggaaggtca tttccacaac atcatcatgc cgaacgtgta catccgaatc ttccccaacg   600
gcaacgtgct gtacagcatc cgaatctccc tgacgctctc gtgccccatg aacctcaagt   660
tgtaccccct ggataagcag acctgctcgc tcaggatggc tagttatggt tggaccacag   720
acgacttagt gttcctatgg aaggaaggcg acccggtgca gg                      762
```

<210> SEQ ID NO 8
<211> LENGTH: 1052
<212> TYPE: DNA
<213> ORGANISM: Heliothis virescens

<400> SEQUENCE: 8

```
cgctctcgtg cccatgaac  ctcaagttgt accccctgga taagcagacc tgctcgctca    60
ggatggctag ttatggttgg accacagacg acttagtgtt cctatggaag gaaggcgacc   120
```

-continued

| | |
|---|---|
| cggtgcaggt ggtgaaaaac ttacacctgc ctcggttcac gctggagaag ttcctcactg | 180 |
| actactgcaa cagtaagact aataccggtg aatacagttg cctgaaggta gacctgctct | 240 |
| tcaaacgcga gctcagttac tacctgatcc agatctacat tccgtgctgc atgctggtca | 300 |
| tcgtgtcctg ggtgtccttc tggctggacc agggagctgt gcctgcgagg gtctcactag | 360 |
| gagtgacgac tttacttaca atggcgaccc agtcgtcagg catcaacgcg tcectaccac | 420 |
| cggtgtccta cacgaaagcc attgatgtct ggactggtgt atgtctcaca ttcgtattcg | 480 |
| gagcgctact agagttcgcg ctcgtcaact atgcgtctcg ctctgacatg caccgagaga | 540 |
| acatgaagaa agcgagacgg gagatggaag cagccagcat ggatgctgcc tcagatctcc | 600 |
| ttgatacaga tagcaacacc acctttgcta tgaaacectt ggtgcgcggc ggcgtggtgg | 660 |
| aatccaagat gcggcagtgc gagatccaca tcaccccgcc gcggaagaac tgctgccgcc | 720 |
| tgtggatgtc caagttcccc acgcgctcca agaggataga cgtcatctcc aggatcacct | 780 |
| tcccacttgt gttcgctctg tttaacctgg cttactgaat gaagcagaga aactcctcct | 840 |
| ttgcgcacag aaatcctgaa gagactgaac aacgaagttt cctaaccaca atcattgcta | 900 |
| tgattatacc gagaatttat tttatactaa ttgttgtgac cacacggttt taacgtagct | 960 |
| tggatccacg cggtgttaat atttgttgat cgcttagaat aaataaatat gctttgttga | 1020 |
| aaaaaaaaaa aaaaaaaaa aaaaaaaaaa aa | 1052 |

<210> SEQ ID NO 9
<211> LENGTH: 28
<212> TYPE: DNA
<213> ORGANISM: Artificial Sequence
<220> FEATURE:
<223> OTHER INFORMATION: Oligonucleotide Gene Specific Primer 1 (GSP1)

<400> SEQUENCE: 9
gctgagcatt gcgaactacg ccttcaac     28

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide Gene Specific Primer 2 (GSP2)

<400> SEQUENCE: 10
taacaccgcg tggatccaag ctacg     25

<210> SEQ ID NO 11
<211> LENGTH: 1609
<212> TYPE: DNA
<213> ORGANISM: Artificial Sequence
<220> FEATURE:
<223> OTHER INFORMATION: PCR amplified fragment of Heliothis DNA cloned
      into pCR2.1-TOPO vector (Invitrogen)

<400> SEQUENCE: 11

| | |
|---|---|
| ctgagcattg cgaactacgc cttcaacatt gtttctttaa acaaacaccg ttttttaatt | 60 |
| ttaatagcac tcattaaagg tttttatttga aggaaagttg tgacagcaac cggagtcgtt | 120 |
| tagaatggga ctttgttgag tcggaggatg gacatcccgc ggccatcatg cgccctcgta | 180 |
| ttggtgttgt tatttgtcac ccatctctca gaatgcatga acggtgggaa gatcaacttt | 240 |
| cgagagaagg agaagcagat cctggatcag atcctgggcc ccgggaggta cgacgccagg | 300 |
| atcagaccct cggggatcaa cggcactgat gggccagcgg tagtgagcgt caatatattt | 360 |

-continued

```
gtccgaagta tatcaaagat cgatgacgtc acaatggaat actccgtaca attaacgttt    420
cgggaacaat ggttagatga acggctcaaa ttcaataatc ttggaggtcg cctcaaatac    480
ctgacactga ctgaagccaa cagagtctgg atgcctgatc tattcttctc caacgagaag    540
gaaggtcatt tccacaacat catcatgccg aacgtgtaca tccgaatctt ccccaacggc    600
aacgtgctgt acagcatccg aatctccctg acgctctcgt gccccatgaa cctcaagttg    660
taccccctgg ataagcagac ctgctcgctc aggatggcta gttatggttg gaccacagac    720
gacttagtgt tcctatggaa ggaaggcgac ccggtgcagg tggtgaaaaa cttacacctg    780
cctcggttca cgctggagaa gttcctcact gactactgca acagtaagac taataccggt    840
gaatacagtt gcctgaaggt agacctgctc ttcaaacgcg agttcagtta ctacctgatc    900
cagatctaca ttccgtgctg catgctggtc atcgtgtcct gggtgtcctt ctggctggac    960
cagggagctg tgcctgcgag ggtctcacta ggagtgacga cttttacttac aatggcgacc   1020 cagtcgtcag gcatcaacgc gtccctacca ccggtgtcct acacgaaagc cattgatgtc   1080
tggactgggt tatgtctcac attcgtattc ggagcgctac tagagtttgc gctcgtcaac   1140
tatgcgtctc gctctgacat gcaccgagag aacatgaaga aagcgagacg ggagatggaa   1200
gcagccagca tggatgctgc ctcagatctc cttgatacag atagcaacac cacctttgct   1260
atgaaaccct tggtgcgcgg cggcgtggtg aatccaaga tgcggcagtg cgagatccac    1320
atcaccccgc cgcggaagaa ctgctgccgc ctgtggatgt ccaagttccc cacgcgctcc   1380
aagaggatag acgtcatctc caggatcacc ttcccacttg tgttcgctct gtttaacctg   1440
gcttactgaa tgaagcagag aaactcctcc tttgcgcaca gaaatcctga agagactgaa   1500
caacgaagtt tcctaaccac aatcattgct atgattatac cgagaattta ttttatacta   1560
attgttgtga ccacacggtt ttaacgtagc ttggatccac gcggtgtta               1609
```

<210> SEQ ID NO 12
<211> LENGTH: 1640
<212> TYPE: DNA
<213> ORGANISM: Artificial Sequence
<220> FEATURE:
<223> OTHER INFORMATION: PCR amplified fragment of Heliothis DNA cloned
  into pCR2.1-TOPO vector (Invitrogen)

<400> SEQUENCE: 12

```
aggtgcggac gtctgcactt gcgaatcgaa gtgatagaaa atagttcgat gaatacggga     60
gtttgagtgg agtgatttat aattcggagg atggacatcc cgcggccatc atgcgccctc    120
gtattggtgt tgttatttgt cacccatctc tcagaatgca tgaacggtgg aagatcaac    180 tttcgagaga aggagaagca gatcctggat cagatcctgg gccccgggag gtacgacgcc    240
aggatcagac cctcggggat caacggcact ggctatgcgc aacgttagt ccatgtcaac    300 atgtatctac ggtccatcag caaaatagat gattacaaaa tggaatactc cgtacaatta    360
acgtttcggg aacaatggtt agatgaacgg ctcaaattca ataatcttgg aggtcgcctc    420
aaatacctga cactgactga agccaacaga gtctggatgc ctgatctatt cttctccaac    480
gagaaggaag tcatttcca caacatcatc atgccgaacg tgtacatccg atcttcccc    540 aacggcaacg tgctgtacag catccgaatc tccctgacgc tctcgtgccc catgaacctc    600
aagttgtacc ccctggataa gcagacctgc tcgctcagga tggctagtta tggttggacc    660
acagacgact agtgttcct atggaaggaa ggcgacccgg tgcaggtggt gaaaaactta   720
cacctgcctc ggttcacgct ggagaagttc ctcactgact actgcaacag taagactaat   780
```

-continued

```
accggtgaat acagttgcct gaaggtagac ctgctcttca aacgcgagtt cagttactac    840
ctgatccaga tctacattcc gtgctgcatg ctggtcatcg tgtcctgggt gtccttctgg    900
ctggaccagg gagctgtgcc tgcgagggtc tcactaggag tgacgacttt acttacaatg    960
gcgacccagt cgtcaggcat caacgcgtcc ctaccaccgg tgtcctacac gaaagccatt   1020
gatgtctgga ctgggttatg tctcacattc gtattcggag cgctactaga gtttgcgctc   1080
gtcaactatg cgtctcgctc tgacatgcac cgagagaaca tgaagaaagc gagacgggag   1140
atggaagcag ccagcatgga tgctgcctca gatctccttg atacagatag caacaccacc   1200
tttgctatga aacccttggt gcgcggcggc gtggtggaat ccaagatgcg gcagtgcgag   1260
atccacatca ccccgccgcg gaagaactgc tgccgcctgt ggatgtccaa gttccccacg   1320
cgctccaaga ggatagacgt catctccagg atcaccttcc cacttgtgtt cgctctgttt   1380
aacctggctt actgttgggg gggcaagagg ggggcggtgg ctgctaccat gtcttgcagg   1440
agcgatgaga ctattaatgc tatttataag ctgatacaga atgaagcaga gaaactcctc   1500
ctttgcgcac agaaatcctg aagagactga acaacgaagt tcctaaccaa caatcattgc   1560
tatgattata ccgagaattt attttatact aattgttgtg accacacggt tttaagctag   1620
cttggatcca cgcggtgtta                                                1640
```

<210> SEQ ID NO 13
<211> LENGTH: 4621
<212> TYPE: DNA
<213> ORGANISM: Heliothis virescens
<220> FEATURE:
<221> NAME/KEY: unsure
<222> LOCATION: (764)...(764)
<223> OTHER INFORMATION: n is a, t, g, or c

<400> SEQUENCE: 13

```
accaggcgaa ctacgccttc aacattgttt ttttaaacaa acaccgtttt ttaatttaa     60
tagctctcat taaaggtttt atttgaagga aagttgtgac agcaaccgga gtcgtttaga   120
atgggacttt gttgagtcgg aggatggaca tcccgcggcc atcatgcgcc ctcgtattgg   180
tgttgttatt tgtcacccat ctctcagaat gcatgaacgg tgggaagatc aactttcgag   240
agaaggagaa gcagatcctg gatcagatcc tgggccccgg gaggtacgac gccaggatca   300
gaccctcggg gatcaacggc actgatgggc cagcggtagt gagcgtcaat atatttgtcc   360
gaagtatatc aaagatcgat gacgtcacaa tggaatactc cgtacagtta acgtttcggg   420
aacaatggtt agatgaacgg ctcaaattca ataatcttgg aggtcgcctc aaatacctga   480
cactgaccga agccaacaga gtctggatgc ctgatctatt cttctccaac gagaaggaag   540
gtcatttcca caacatcatc atgccgaacg tgtacatccg gatcttcccc aacggcaacg   600
tgctgtacag catccgaatc tccttgacgc tctcgtgccc catgaacctc aagttgtacc   660
ccctggataa gcagacctgc tcgctcagga tggctagtta tggttggacc acagacgact   720
tagtgttcct atggaaggaa ggcgacccgg tgcaggtggt gaanaactta cacctgcctc   780
ggttcacgct ggagaagttc ctcactgact actgcaacag taagactaat accggtgaat   840
acagttgcct gaaggtagac ttgctcttca aacgcgagtt cagttactac ctgatccaga   900
tctacattcc gtgctgcatg ctggtcatcg tgtcctgggt gtccttctgg ctggaccagg   960
gagctgtgcc tgcgagggtc tcactaggag tgacgacttt acttacaatg gcgacccagt  1020
cgtcaggcat caacgcgtcc ctaccaccgg tgtcctacac gaaagccatt gacgtctgga  1080
ctggtgtatg tctcacattc gtattcggag cgctactaga gttcgcgctc gtcaactatg  1140
```

-continued

```
cgtctcgctc tgacatgcac cgagagaaca tgaagaaagc gagacgggag atggaagcag    1200
ccagcatgga tgctgcctca gatctcctag acacagatag caacaccacc tttgctatga    1260 aaccccttggt gcgcggcggc gtggtggaat ccaagatgcg gcagtgcgag atccacatca    1320
ccccgccgcg gaagaactgc tgccgcctgt ggatgtccaa gttccccacg cgctccaaga    1380
ggatagacgt catctccagg atcaccttcc cacttgtgtt cgctctgttt aacctggctt    1440
actggtcgac gtacctgttc cgcgacgagg acgaggagaa gtgattctcc gagtccctgg    1500 agagggggcgt ggggccgcgc gtgcagctgg tggcggccgt cgtgatgccc tacgtgctgt    1560
tcgtggtggc gtactcgctg tgcttccgcg cgcgcgcccc gccccttcg ccccgcccg     1620 cgcccgcgcc cgcgcccgcg cccgcaccct cccgccgcag cgcgcgcgca cgcacacaag    1680
cacacccacc tagcccgctc tagcgaactc accccattca ttatcgtgac atattatatt    1740
atcgtgtatt ttaatcgacg tcttcctcgt ggcagcgtta ttcccactca gtattcgatg    1800
gcgttagtgt aattagtaaa gctcaagtgt ctatttgtat atatatgtga ccccccgtgcc    1860 agtttagacc aagcctccgt ttttaaattg aagcagttcg agaaaaacgg taaaaataga    1920
ctcaattttg attggtcatc taaacagcag aacttttatt cggcacttat aaagtcctca    1980 attattgtg tacaaaaata aatattttac tttccgagaa ttaaaaattt tcgataattt    2040
taccaatgat atgactcctt gtatggattc gtatgtaatg taaacctagg ttaagatata    2100
agaggaatcc cagaggttcc cgcatattac tttagccttt aaagtaaggt aaataaggac    2160
tagaatggca ctaatgtgta gtggaagtgg ggtattattt agtagttttc actctacagt    2220
acgtgaactg gactagatct actagcaaat agagttgatc aattttcatg tcgaaatgtt    2280
cacagatatt gtataaaccg ctggaggtaa acagctatca acaatgtaac accaaatacc    2340 atcgaatca agcaaaacca tggaaatttt gctaatcgaa aagttgtaac tgtttatcta    2400
tggcaggtat aattggccta gtaatgtatc gtgtagtatc atttacaaca catattaact    2460
attaaccaca ttatgtgaaa gaaggaattt ataaaaaaaa ccttattaaa tatatattag    2520
ataagtatta ttaattggat attctcttgc tggggatttt aatatgaatc ttacctttaa    2580
ataagtttga tctcactaga cgttgcaaat ggatacccca aatacctttt ccgcattaaa    2640
aggtattatt ttaacaaatg tattcttccc cgtcaatgtt ttaagactac gtatctacat    2700
aaaatgatgt attgttcata caatactatt tcaaaatgca agaacaacgt aaagtgcatt    2760
tcattgatgt ttgtgtatgt agatgacatt agtattttac ccaaaaatac tgatattaaa    2820
attcccagta agattcgtag gtaaatggta aacgtgtaaa tagttgggcc tacaactttc    2880
tacacctgtg tcgctcagtg tacagttacc tatatttaat attacaatta tatcattatt    2940
aacgaatgat aagatttat taacattaat ttctctgtct gaacgtatca ctgtaaatat    3000
tactaaatgt ttcctaatta cattattcat acatatatta tcatcccttg agctatagtt    3060
gcaaagtatt ccaaaccac aatgaaaata aatttcaat ttacttcacg atcaccaaat    3120
tgtgaaaacc tggttgttct gaattcattt aacaattagt ttttactttg aatccatggc    3180
tcaagggaca tcctaaggat attcattgaa atctatttag aatctcgtgt atgtatcatg    3240
acaccttcaa ataaaatatc actaatgctg tgttcggcta ttagatacaa taagtcgtac    3300
atattaacgt aagcacattc gttttttatta tgcggcggag agaacgcatc tgtttctata    3360
acgaaagggt ggccattatc ggctatatca tcttgcttgg tctgtataaa aataagagtc    3420
aaagactcgg gggaaacccc tatatgtata ctatcataac cgttatcctt atttttgacaa    3480
```

-continued

```
agctctggga aacgaaatag cattttgttt caattacaca attcttgctc attttttctct    3540 tccgccttt  attttgaatt  aggtgttgcc cactgtgcgc aatactctaa tggcttagaa     3600
ttatccttaa tatatattct cgggctgtga cgaggtgtag catctgcatt attatattaa    3660
tgtcatttcg tttgccattc gttgtatgta aggaaatatt agcctatgtc caacgctcaa    3720
aatctcatag acgtattagg cacacataag tgtacctttt cgtatgtatg taaattattg    3780
gagactcaat gtcttagttg gtgctatata tactacgatc cgaggagaat gtacccagta    3840
gtttactcat acataacgcc actgatatct tgtggaggaa atattatctg cgagacaagt    3900
agacattagt taagtttaca tatttacaat aaatgtttcc attattagga tataacatat    3960
gaatgtgtta ctgttgaaag cagcttctca aggtaccacc agtaattcgg agatacttgt    4020
aggatttgca ttcgataaac aacttatact aaaacgaaga tttgactgaa tctaaaccgc    4080
aaatactgtg gtcaaaatta ttaaacactt tcaatacatg ttgtacgcat gtttctgtaa    4140
tttcacattt aattgtaaag tcaattaaat cactgtataa taatacattt tcaacatatc    4200
tctcactgtt aagatttcgg ttggtccaac gacagaatca aatcgcaacg taatgatgat    4260
ccgggcaaaa ctaacaacta gatagatctc ttaaatgatt acgttgaagt ggaagaggtg    4320
atgtatgaag gaaggtagga ttaagtaaca ctgtataata tattgaccat aattacgatt    4380
ttagaagtca taatggacgg tttacctctt aagattatac agtaaaggta gatagtttca    4440
ttcgtaagct atgttgtact cgattggtat gacataacta atgactgagc tttgtcatct    4500
actacaaccc gagggcgaat acctccttct tctaccattc ccatttaatt ataaagaaac    4560
attgtaaaaa atgatttaat aaaatatccc aaatatctta aacaaaaaa aaaaaaaaa     4620 a                                                                    4621
```

<210> SEQ ID NO 14
<211> LENGTH: 450
<212> TYPE: PRT
<213> ORGANISM: Heliothis virescens

<400> SEQUENCE: 14

Ser Glu Gln Ile Asp Asn Met Asp Ile Pro Arg Pro Ser Cys Ala Leu
 1               5                  10                  15

Val Leu Leu Phe Val Thr His Leu Ser Glu Cys Met Asn Gly Gly Lys
            20                  25                  30

Ile Asn Phe Arg Glu Lys Glu Lys Gln Ile Leu Asp Gln Ile Leu Gly
        35                  40                  45

Pro Gly Arg Tyr Asp Ala Arg Ile Arg Pro Ser Gly Ile Asn Gly Thr
    50                  55                  60

Asp Gly Pro Ala Val Val Ser Val Asn Ile Phe Val Arg Ser Ile Ser
65                  70                  75                  80

Lys Ile Asp Asp Val Thr Met Glu Tyr Ser Val Gln Leu Thr Phe Arg
                85                  90                  95

Glu Gln Trp Leu Asp Glu Arg Leu Lys Phe Asn Asn Leu Gly Gly Arg
            100                 105                 110

Leu Lys Tyr Leu Thr Leu Thr Glu Ala Asn Arg Val Trp Met Pro Asp
        115                 120                 125

Leu Phe Phe Ser Asn Glu Lys Glu Gly His Phe His Asn Ile Ile Met
    130                 135                 140

Pro Asn Val Tyr Ile Arg Ile Phe Pro Asn Gly Asn Val Leu Tyr Ser
145                 150                 155                 160

Ile Arg Ile Ser Leu Thr Leu Ser Cys Pro Met Asn Leu Lys Leu Tyr

-continued

```
                         165                 170                 175
Pro Leu Asp Lys Gln Thr Cys Ser Leu Arg Met Ala Ser Tyr Gly Trp
            180                 185                 190
Thr Thr Asp Asp Leu Val Phe Leu Trp Lys Glu Gly Asp Pro Val Gln
            195                 200                 205
Val Val Lys Asn Leu His Leu Pro Arg Phe Thr Leu Glu Lys Phe Leu
            210                 215                 220
Thr Asp Tyr Cys Asn Ser Lys Thr Asn Thr Gly Glu Tyr Ser Cys Leu
225                 230                 235                 240
Lys Val Asp Leu Leu Phe Lys Arg Glu Phe Ser Tyr Tyr Leu Ile Gln
            245                 250                 255
Ile Tyr Ile Pro Cys Cys Met Leu Val Ile Val Ser Trp Val Ser Phe
            260                 265                 270
Trp Leu Asp Gln Gly Ala Val Pro Ala Arg Val Leu Leu Gly Val Thr
            275                 280                 285
Thr Leu Leu Thr Met Ala Thr Gln Ser Ser Gly Ile Asn Ala Ser Leu
            290                 295                 300
Pro Pro Val Ser Tyr Thr Lys Ala Ile Asp Val Trp Thr Gly Val Cys
305                 310                 315                 320
Leu Thr Phe Val Phe Gly Ala Leu Leu Glu Ser Arg Phe Val Asn Tyr
            325                 330                 335
Ala Ser Arg Ser Asp Met His Arg Glu Asn Met Lys Lys Ala Arg Arg
            340                 345                 350
Glu Met Glu Ala Ala Ser Met Asp Ala Ala Ser Asp Leu Leu Asp Thr
            355                 360                 365
Asp Ser Asn Thr Thr Phe Ala Met Lys Pro Leu Val Arg Gly Gly Val
370                 375                 380
Val Glu Ser Lys Met Arg Gln Cys Glu Ile His Ile Thr Pro Pro Arg
385                 390                 395                 400
Lys Asn Cys Cys Arg Leu Trp Met Ser Lys Phe Pro Thr Arg Ser Lys
            405                 410                 415
Arg Ile Asp Val Ile Ser Arg Ile Thr Phe Pro Leu Val Phe Ala Leu
            420                 425                 430
Phe Asn Leu Ala Tyr Trp Ser Thr Tyr Leu Phe Arg Asp Glu Asp Glu
            435                 440                 445
Glu Lys
450
```